United States Patent [19]

Nagabhushan et al.

[11] 4,296,242

[45] Oct. 20, 1981

[54] PROCESS FOR THE PREPARATION OF CHIRAL 3-AMINO-2-HYDROXYPROPIONIC ACID AND N-BLOCKED DERIVATIVES THEREOF

[75] Inventors: Tattanahalli L. Nagabhushan, Parsippany; Alan Cooper, West Caldwell, both of N.J.

[73] Assignee: Schering Corporation, Kenilworth, N.J.

[21] Appl. No.: 46,076

[22] Filed: Jun. 6, 1979

[51] Int. Cl.$^3$ ............................................. C07C 101/30
[52] U.S. Cl. .................................... 560/160; 548/232; 548/230; 562/567
[58] Field of Search ................ 562/567, 570; 548/229, 548/230; 536/23; 560/160

[56] References Cited

U.S. PATENT DOCUMENTS

| | | | |
|---|---|---|---|
| 2,530,627 | 11/1950 | Pfister | 562/567 |
| 2,556,791 | 6/1951 | Billman | 562/567 |
| 2,868,801 | 1/1959 | Steele | 548/229 |
| 2,975,187 | 3/1961 | Lynn | 548/229 |
| 3,120,510 | 2/1964 | Steyermark | 536/23 |
| 3,133,932 | 5/1964 | Horn | 548/229 |

FOREIGN PATENT DOCUMENTS

| | | | |
|---|---|---|---|
| 883902 | 7/1953 | Fed. Rep. of Germany | 548/229 |
| 51-16660 | 10/1976 | Japan . | |
| 51-16661 | 10/1976 | Japan . | |

OTHER PUBLICATIONS

Amezawa, Bull. Chem. Soc. Jap., 44, pp. 1411–1415, (1971).

Lemieux, Canadian Journal of Chem., 33, pp. 1701–1719.

Gundermann, Ber. 91, pp. 160–167, (1958).

*Primary Examiner*—Natalie Trousof
*Assistant Examiner*—Michael Shippen
*Attorney, Agent, or Firm*—Mary S. King; Anita W. Magatti; Elizabeth A. Bellamy

[57] ABSTRACT

This invention describes a novel process whereby D-glucose and D-mannose are converted to S-3-amino-2-hydroxypropionic acid and R-3-amino-2-hydroxypropionic acid, respectively, and their N-blocked derivatives.

7 Claims, No Drawings

PROCESS FOR THE PREPARATION OF CHIRAL 3-AMINO-2-HYDROXYPROPIONIC ACID AND N-BLOCKED DERIVATIVES THEREOF

FIELD OF THE INVENTION

This invention relates to a novel process for the conversion of glycoses to chiral 3-amino-2-hydroxypropionic acid which, when N-blocked and converted to an active ester, is reacted with suitable aminoglycoside antibiotics to produce known and active semi-synthetic antibacterial agents.

Specifically, this invention relates to the conversion of D-glucose or D-mannose to S or R-3-(N-blocked amino)-2-hydroxypropionic acid active ester which may be reacted, for example, with a 1-N-unsubstituted poly-N-blocked aminoglycoside, and the resultant compound deblocked to produce 1-N-(S or R-3-amino-2-hydroxypropionyl) aminoglycoside antibiotics.

Particularly, this invention relates to the process for converting D-glucamine or D-mannamine to S-3-amino-2-hydroxypropionic acid or R-3-amino-2-hydroxypropionic acid, otherwise known as S-isoserine or R-isoserine, respectively.

Prior Art

There are a number of methods for the preparation of S-isoserine or R-isoserine, for example, Ber. 47 (2027) 1914, Japanese patents Kokai 74,135,922 and Kokai 7,537,723 to name just a few. In the Ber. reference, resolution requiring the use of brucine salts is part of the process. In the 74,135,922 patent, the products are the result of a fermentation and in the 7,537,723 patent, the starting material, L-asparagine, is expensive and the isolation of the end product is tedious.

Process Aspect of the Invention

The process aspect of this invention resides in the concept of preparing chiral 3-amino-2-hydroxypropionic acid which comprises subjecting a glycamine in an aqueous lower alkanol medium to the successive steps of
(a) cyclic 1,2-N,O-carbonylation,
(b) periodic cleavage,
(c) permanganate oxidation,
(d) acid hydrolysis, followed by
(e) treatment with base.

Chiral (i.e., S or R) 3-amino-2-hydroxypropionic acid, otherwise known as S-isoserine or R-isoserine, also referred to as S-HAPA or R-HAPA, have found usefulness in the preparation of important aminoglycoside antibiotics, for example, 1-N-S-HAPA-gentamicin B or 1N-R-HAPA-gentamicin B. The preparation of these compounds are described in U.S. Pat. No. 4,136,254.

However, as disclosed in the above cited references, the previous methods of preparing the chiral isoserines either utilized materials with (a) toxicity problems, e.g., brucine salts, (b) fermentation methods, or (c) expensive and tedious reactions.

By our novel method, S- or R-HAPA may be prepared from various glycoses. The S- or R-HAPA's may be prepared as the free amino acids, the acid addition salts or alternatively, as the S- or R-N-blocked HAPA's which compounds would be more generally useful in the preparation of the N-substituted aminoglycoside antibiotics. The best known examples of the latter being those wherein the S- or R-HAPA moiety is at the 1-amino position.

The glycoses employed for the obtention of the starting materials of our inventive process are those known in the art, e.g., D-glucose, D-mannose, D-ribose, D-arabinose, etc. The glycoses are converted first to their respective glycamines. For example, via processes described in U.S. Pat. Nos. 2,621,175 and 2,830,983, D-glucose can be catalytically reduced to D-glucamine; analogously, D-mannose can be converted to D-mannamine; D-ribose, converted to D-ribamine; D-arabinose to D-arabinamine, etc. Preferentially, we utilize D-glucose and D-mannose as starting materials due to their availability and inexpensiveness.

It will be obvious to those skilled in the art that the starting glycose will determine the resultant chiral form. The following Flow Chart I is illustrative of our process in the conversion of D-glucamine to the S-HAPA or, indeed, to its N-blocked derivative. Inherent in this pictoral representation is that D-mannamine can similarly be converted to R-HAPA or its N-blocked derivative.

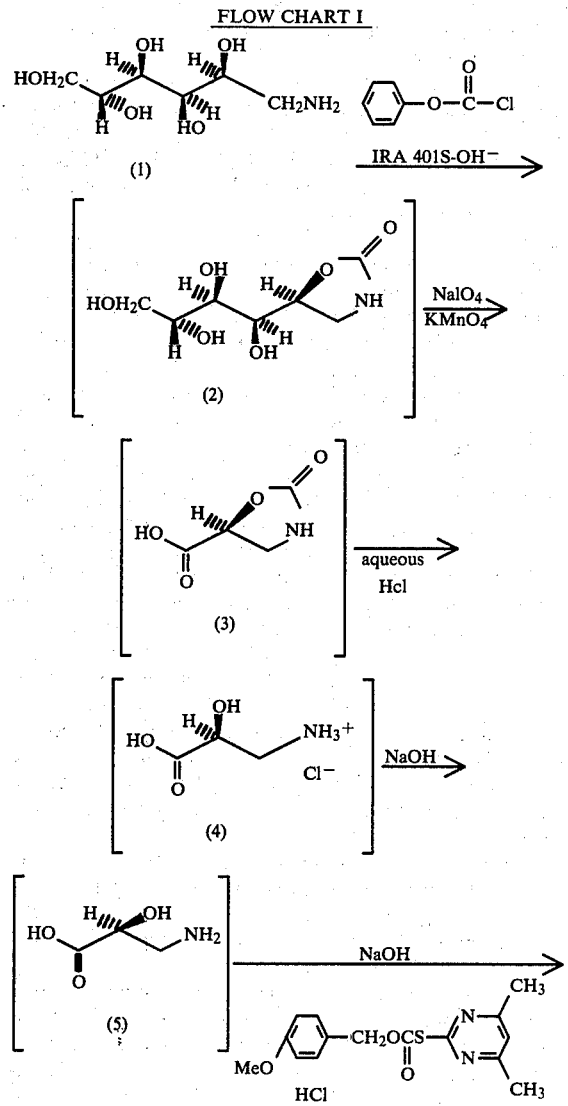

FLOW CHART I

-continued
FLOW CHART I

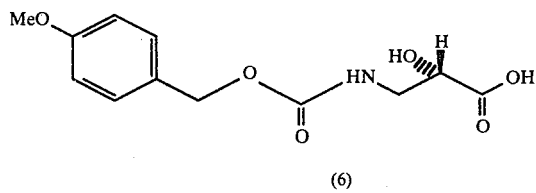

(6)

Flow Chart I is illustrative of the process of subjecting D-glucamine in an aqueous lower alkanol medium to the successive steps of (a) 1,2-N,O-cabonylation to produce 1,2-N,O-carbonyl-D-glucamine (compound 2), (b) periodic cleavage, (c) permanganate oxidation to produce S-2,3-N,O-carbonylisoserine (compound 3), (d) acid hydrolysis to produce an acid addition salt of S-isoserine (compound 4), and (e) treatment with base to neutralize the acid addition salt to produce S-isoserine (compound 5).

S-isoserine, when utilized as a moiety to be attached to an aminoglycoside, is usually suitably N-blocked. Therefore, Flow Chart I is further illustrative that, alternatively, the acid addition salt may be treated with sufficient base as a prelude to the subsequent step of conversion to a S-(N-blocked)-isoserine, in the above instance, the p-methoxybenzyloxycarbonylamino derivative (compound 6).

It is inherent within the illustrative aegis of Flow Chart I that when D-mannamine is substituted for D-glucamine, compound 2 will be 1,2-N,O-carbonyl-D-mannamine, compound 3 will be R-2,3-N,O-carbonylisoserine, compound 4 will be an acid addition salt of R-isoserine, and compound 5 will be R-isoserine. As in the case of S-isoserine, a subsequent step may be employed to obtain compound 6, e.g., R-N-(p-methoxybenzyloxycarbonyl)isoserine.

Included among the lower alkanols useful for our reaction medium are those which will preferentially, but not necessarily, form a 50:50 mixture with water, i.e., those alkanols having from 1 to 3 carbon atoms.

The cyclic 1,2-N,O-carbonylation is effected with a hydrocarbonoxycarbonylchloride or phosgene. The hydrocarbonoxycarbonylchloride reactants that we contemplate are alkoxycarbonylchloride such as methoxycarbonylchloride, phenoxycarbonylchloride, substituted phenoxycarbonylchloride such as p-nitrophenoxycarbonylchloride. It will be obvious to those skilled in the art that reaction conditions may differ slightly dependent on which of the aforementioned reactants are used.

The periodic cleavage is effected with an alkali metal salt metaperiodate such as the sodium, potassium, calcium and ammonium metaperiodates. Under the conditions of utilizing an alkali metal salt metaperiodate, we utilize potassium permanganate as the oxidizing agent. This combination being the art recognized Lemieux oxidation.

Among the aqueous mineral acids we contemplate are hydrochloric, sulfuric, hydrogen bromide and phosphoric. Among the bases used for base treatment are the alkali metal hydroxides or carbonates such as sodium, potassium and calcium.

Among the amino protecting groups contemplated in the subsequent steps of conversion to a S- or R-N-(blocked/protected)-isoserine are Schiff's bases, amides (e.g., phthalimido, succinimido) and acyl groups, particularly p-methoxybenzyloxycarbonyl, benzyloxycarbonyl, 2,2,2-trichloroethoxycarbonyl, t-butoxycarbonyl, t-amyloxycarbonyl and acetyl. The foregoing blocking groups and the corresponding blocking group reagents whereby they are formed are well known in the art.

The invention described hereinabove is illustrated in detail hereinbelow in the Examples, and should not be construed as limiting the scope of our invention.

EXAMPLE I

S or R-3-(N-Blocked)Amino-2-Hydroxypropionic Acid

A.
S-3-p-Methoxybenzyloxycarbonylamino-2-hydroxypropionic Acid

Dissolve 9.05 g D-glucamine (50 mmole) in 140 ml of 50% aqueous methanol. Add with stirring, in a moderately rapid dropwise manner, 7.5 ml of phenylchloroformate. Immediately after the addition bring the pH to $8\pm0.5$ by the addition of Amberlite IRA-401S OH$^-$ ion exchange resin. Maintain this pH for an additional 1 hour and then remove the resin by filtration, wash with water three times ($3\times100$ ml). Extract the aqueous solution once with ethyl acetate (100 ml) and evaporate off the methanol. Dilute the aqueous layer to 500 ml with water.

Add with stirring 32 g sodium metaperiodate and adjust the pH to 6.0 with the addition of a saturated solution of potassium carbonate. Stir for 15 minutes and then adjust the pH to 7.7 with potassium carbonate. Add 15.8 g of potassium permanganate. Maintain the pH at 7.7 for 1 hour and then let the pH rise. After 15 hours stirring remove the solids by filtration, wash with water (200 ml), and (after checking with starch-iodide paper) evaporate the solution to a residue. Extract by triturating the residue three times with a solvent mixture composed of chloroform, methanol and ammonium hydroxide (3:4:2) ($3\times150$ ml). Evaporate the solvents in vacuo to a residue. Dissolve the residue in 4 N hydrochloric acid (100 ml) and heat to reflux for 15 hours. Cool to 45° C. and concentrate to dryness in vacuo. Dissolve the residue in water (125 ml) and adjust the pH to 9 with 20% sodium hydroxide solution. Add dioxane (125 ml) and stir. Add dropwise a solution of p-methoxybenzyl S-(4,6-dimethyl-pyrimidin-2-yl)-thiolcarbonate (14.8 g) in dioxane (70 ml). Maintain the pH at 9.0 with the addition of potassium carbonate. After 2 hours, evaporate the mixture in vacuo to remove dioxane and extract the water solution with ethyl acetate (100 ml). Acidify the aqueous layer to pH 2 with 4 N hydrochloric acid with stirring. Extract the acidified solution with ethyl acetate ($3\times200$ ml), washed the combined organic layer with 1 N hydrochloric acid (100 ml). Dry the ethyl acetate layer over anhydrous magnesium sulfate, filter and evaporate to a solid residue in vacuo. Recrystallize the residue by dissolving in boiling chloroform (50 ml) to obtain the named compound; m.p. 137°–138°, $[\alpha]_D^{26}+3.1°$ (c, 0.5 in methanol).

B.
R-3-p-Methoxybenzylcarbonylamino-2-Hydroxypropionic Acid

In a manner similar to Example IA, by substituting D-mannamine for D-glucamine, there is obtained the above-named compound.

C. S-3-(2,2,2-Trichloroethoxycarbonylamino)-2-Hydroxypropionic Acid

Dissolve 9.05 g D-glucamine (50 mmole) in 140 ml of 50% aqueous methanol. Add with stirring, in a moderately rapid dropwise manner, 7.5 ml of phenylchloroformate. Immediately after the addition bring the pH to 8±0.5 by the addition of Amberlite IRA-401S OH⁻ ion exchange resin. Maintain this pH for an additional 1 hour and then remove the resin by filtration, wash with water three times (3×100 ml). Extract the aqueous solution once with ethyl acetate (100 ml) and evaporate off the methanol. Dilute the aqueous layer to 500 ml with water.

Add with stirring 32 g sodium metaperiodate and adjust the pH to 6.0 with the addition of a saturated solution of potassium carbonate. Stir for 15 minutes and then adjust the pH to 7.7 with potassium carbonate. Add 15.8 g of potassium permanganate. Maintain the pH at 7.7 for 1 hour and then let the pH rise. After 15 hours stirring, remove the solids by filtration, wash with water (200 ml) and (after checking with starch-iodide paper) evaporate the solution to a residue. Extract by triturating the residue three times with a solvent mixture composed of chloroform, methanol and ammonium hydroxide (3:4:2) (3×150 ml). Evaporate the solvents in vacuo to a residue. Dissolve the residue in 4 N hydrochloric acid (100 ml) and heat to reflux for 15 hours. Cool to 45° C. and concentrate to dryness in vacuo. Dissolve the residue in water (125 ml) and adjust the pH to 9 with 20% sodium hydroxide solution. Add dioxane (125 ml) and stir, and then add, dropwise, a solution of 2,2,2-trichloroethoxycarbonylchloride (6.83 ml) in 10 ml of dioxane. Stir and maintain the pH at 9.0 with potassium carbonate. After 2 hours, evaporate the mixture in vacuo to remove dioxane and extract the water solution with ethyl acetate (100 ml). Acidify the aqueous layer to pH 2 with 4 N hydrochloric acid with stirring. Extract the acidified solution with ethyl acetate (3×200 ml). Dry the ethyl acetate layer over anhydrous magnesium sulfate, filter and evaporate to a solid residue in vacuo. Recrystallize the residue by dissolving in boiling chloroform (50 ml) to obtain the named compound; m.p. 100°–107° C., $[\alpha]_D^{26}+4.9°$ (c, 0.6 in methanol).

D. R-3-(2,2,2-Trichloroethoxycarbonylamino)-2-Hydroxypropionic Acid

In a manner similar to Example IC, by substituting D-mannamine for D-glucamine, there is obtained the above-named compound.

EXAMPLE II

S or R-3-Amino-2-Hydroxypropionic Acid

A. S-3-Amino-2-Hydroxypropionic Acid

Dissolve 9.05 g D-glucamine (50 mmole) in 140 ml of 50% aqueous methanol. Add with stirring, in a moderately rapid dropwise manner, 7.5 ml of phenylchloroformate. Immediately after the addition bring the pH to 8±0.5 by the addition of Amberlite IRA-401S OH⁻ ion exchange resin. Maintain this pH for an additional 1 hour and then remove the resin by filtration, wash with water three times (3×100 ml). Extract the aqueous solution once with ethyl acetate (100 ml) and evaporate off the methanol. Dilute the aqueous layer to 500 ml with water.

Add with stirring 32 g sodium metaperiodate and adjust the pH to 6.0 with the addition of a saturated solution of potassium carbonate. Stir for 15 minutes and then adjust the pH to 7.7 with potassium carbonate. Add 15.8 g of potassium permanganate. Maintain the pH at 7.7 for 1 hour and then let the pH rise. After 15 hours stirring, remove the solids by filtrations, wash with water (200 ml) and (after checking with starch-iodide paper) evaporate the solution to a residue. Extract by triturating the residue three times with a solvent mixture composed of chloroform, methanol and ammonium hydroxide (3:4:2) (3×150 ml). Evaporate the solvents in vacuo to a residue. Dissolve the residue in 4 N hydrochloric acid (100 ml) and heat to reflux for 15 hours. Cool to 45° C. and concentrate to dryness in vacuo. Dissolve the residue in a minimum amount of water, neutralized to pH 4 with dilute sodium hydroxide, and add to a column consisting of 500 gms. of Amberlite IRC-50 (H+), and fractionate the column with 3 liters of water. Evaporate the homogeneous fractions to obtain the pure product S-3-amino-2-hydroxypropionic acid as a residue.

B. R-3-Amino-2-Hydroxypropionic Acid

In a manner similar to Example IIA, by substituting D-mannamine for D-glucamine, there is obtained the above-named compound.

We claim:

1. The process of preparing chiral 3-amino-2-hydroxypropionic acid which comprises subjecting a glycamine in an aqueous lower alkanol medium to the successive steps of
   (a) cyclic 1,2-N,O-carbonylation with alkoxycarbonyl chloride, phenoxycarbonyl chloride, or p-nitrophenoxycarbonyl chloride to produce the corresponding chiral 1,2-N,O-carbonyl glycamine,
   (b) periodic cleavage, and (c) permanganate oxidation to produce chiral 2,3-N,O-carbonylisoserine,
   (d) acid hydrolysis to produce an acid addition salt of chiral isoserine, followed by
   (e) treatment with base to neutralize the acid addition salt to produce chiral isoserine.

2. The process of claim 1 wherein the glycamine is D-glucamine or D-mannamine.

3. The process of claim 2 which comprises subjecting D-glucamine in an aqueous lower alkanol medium to the successive steps of
   (a) 1,2-N,O-carbonylation to produce 1,2-N,O-carbonyl-D-glucamine,
   (b) periodic cleavage and (c) permanganate oxidation to produce S-2,3-N,O-carbonylisoserine,
   (d) acid hydrolysis to produce an acid addition salt of S-isoserine, followed by
   (e) treatment with base to neutralize the acid addition salt to produce S-isoserine, 4. The process of claim 2 which comprises subjecting D-mannamine in an aqueous lower alkanol medium to the successive steps of
   (a) 1,2-N,O-carbonylation to produce 1,2-N,O-carbonyl-D-mannamine,
   (b) periodic cleavage and (c) permanganate oxidation to produce R-2,3-N,O-carbonylisoserine,
   (d) acid hydrolysis to produce an acid addition salt of R-isoserine, followed by
   (e) treatment with base to neutralize the acid addition salt to produce R-isoserine.

5. The process of claim 3 or claim 4 wherein said successive steps of
   (a) cyclic 1,2-N,O-carbonylation is effected with a alkoxycarbonyl chloride, phenoxycarbonyl chloride, or p-nitrophenoxycarbonyl chloride or phosgene.
   (b) periodic cleavage is effected with sodium metaperiodate, potassium metaperiodate, calcium metaperiodate and ammonium metaperiodate,
   (c) oxidation is effected with potassium permanganate,
   (d) acid hydrolysis is effected with an aqueous mineral acid, and
   (e) treatment with base is effected with sodium hydroxide, potassium hydroxide, calcium hydroxide, sodium carbonate, potassium carbonate and calcium carbonate.

6. The process of claim 5 wherein said aqueous mineral acid is hydrochloric, sulfuric, hydrogen bromide and phosphoric.

7. The process of preparing N-protected chiral 3-amino-2-hydroxypropionic acid which comprises subjecting a glycamine in an aqueous lower alkanol medium to the successive steps of
   (a) cyclic 1,2-N,O-carbonylation with alkoxycarbonyl chloride, phenoxycarbonyl chloride, or p-nitrophenoxycarbonyl chloride to produce the corresponding chiral 1,2-N,O-carbonyl glycamine,
   (b) periodic cleavage, and (c) permanganate oxidation to produce chiral 1,2-N-carbonylisoserine,
   (d) acid hydrolysis to produce an acid addition salt of chiral isoserine.
   (e) treatment with base to neutralize the acid addition salt to produce chiral isoserine, and
   (f) the reaction of an amino protecting group reagent with chiral isoserine to produce N-protected chiral isoserine wherein said amino protecting group is selected from the group consisting of p-methoxybenzyloxycarbonyl, benzyloxycarbonyl 2,2,2-trichloroethoxycarbonyl, t-butoxycarbonyl, t-amyloxycarbonyl and acetyl.

* * * * *